United States Patent
Troetzschel et al.

(10) Patent No.: US 10,290,400 B2
(45) Date of Patent: May 14, 2019

(54) METHOD OF PRODUCING A CERMET-CONTAINING BUSHING FOR AN IMPLANTABLE MEDICAL DEVICE

(71) Applicant: Heraeus Deutschland GmbH & Co. KG, Hanau (DE)

(72) Inventors: Jens Troetzschel, Ronneburg (DE); Heiko Specht, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 2 days.

(21) Appl. No.: 15/279,344

(22) Filed: Sep. 28, 2016

(65) Prior Publication Data

US 2017/0018337 A1    Jan. 19, 2017

Related U.S. Application Data

(62) Division of application No. 14/171,275, filed on Feb. 3, 2014, now Pat. No. 9,480,168, and a division of
(Continued)

(30) Foreign Application Priority Data

Aug. 4, 2009    (DE) .................. 10 2009 035 972

(51) Int. Cl.
    *H01B 19/00*    (2006.01)
    *H01B 17/30*    (2006.01)
    (Continued)

(52) U.S. Cl.
    CPC ......... *H01B 17/306* (2013.01); *A61N 1/3754* (2013.01); *H01B 13/0036* (2013.01);
(Continued)

(58) Field of Classification Search
    CPC ......... Y10T 29/49227; Y10T 29/49117; Y10T 29/49158; Y10T 29/49163;
(Continued)

(56) References Cited

U.S. PATENT DOCUMENTS

| 4,352,951 A | 10/1982 | Kyle |
| 4,362,792 A | 12/1982 | Bowsky et al. |

(Continued)

FOREIGN PATENT DOCUMENTS

| DE | 697 297 19 | 7/2005 |
| DE | 102009035971 | 2/2011 |
| DE | 102009035972 | 4/2011 |

OTHER PUBLICATIONS

The Office Action for U.S. Appl. No. 12/850,406 dated Sep. 17, 2012 (11 pages).
(Continued)

*Primary Examiner* — Thiem D Phan
(74) *Attorney, Agent, or Firm* — Dicke, Billig & Czaja, PLLC

(57) ABSTRACT

One aspect relates to a method for producing an electrical bushing for an implantable medical device. The method includes forming a holding element for holding the electrical bushing in the implantable medical device, the holding element including a through-opening. An insulation element of aluminum oxide is formed within the through-opening. At least one elongated conduction element is formed extending through insulation element. The at least one elongated conduction element includes an aluminum oxide in a metallic matrix. The insulation element and the at least one elongated conduction element are jointly fired thereby forming a hermetic seal therebetween without welding or soldering.

10 Claims, 2 Drawing Sheets

Related U.S. Application Data application No. 12/850,406, filed on Aug. 4, 2010, now Pat. No. 8,755,887.

(51) Int. Cl.
*A61N 1/375* (2006.01)
*H05K 3/30* (2006.01)
*H01B 13/00* (2006.01)

(52) U.S. Cl.
CPC .............. *H01B 19/00* (2013.01); *H05K 3/30* (2013.01); *Y10T 29/4913* (2015.01); *Y10T 29/49227* (2015.01)

(58) Field of Classification Search
CPC .. Y10T 29/49204; H01B 19/00; H01B 13/00; H01B 17/305
USPC ... 29/887, 860, 592.1, 594, 602.1, 825, 832, 29/848, 851; 607/5, 9, 36, 37, 53, 54, 607/115, 116; 174/650, 659
See application file for complete search history.

(56) References Cited

U.S. PATENT DOCUMENTS

| | | | |
|---|---|---|---|
| 4,456,786 A | 6/1984 | Kyle | |
| 4,488,673 A | 12/1984 | Hopper, Jr. | |
| 4,678,868 A | 7/1987 | Kraska et al. | |
| 4,737,601 A | 4/1988 | Gartzke | |
| 4,774,953 A | 10/1988 | Foote | |
| 4,816,621 A | 3/1989 | Huebner et al. | |
| 4,991,582 A | 2/1991 | Byers et al. | |
| 4,992,910 A | 2/1991 | Evans | |
| 5,046,262 A | 9/1991 | Kerbaugh | |
| 5,245,999 A | 9/1993 | Dahlberg et al. | |
| 5,272,283 A | 12/1993 | Kuzma | |
| 5,513,793 A | 5/1996 | Malmgren | |
| 5,654,106 A | 8/1997 | Purnell et al. | |
| 5,683,435 A | 11/1997 | Truex et al. | |
| 5,738,270 A | 4/1998 | Malmgren | |
| 5,750,926 A | 5/1998 | Schulman et al. | |
| 5,769,874 A | 6/1998 | Dahlberg | |
| 5,782,891 A | 7/1998 | Hassler et al. | |
| 5,821,011 A | 10/1998 | Taylor et al. | |
| 5,851,222 A | 12/1998 | Taylor et al. | |
| 5,855,711 A | 1/1999 | Araki et al. | |
| 5,861,714 A | 1/1999 | Wei et al. | |
| 5,866,851 A | 2/1999 | Taylor et al. | |
| 6,090,503 A * | 7/2000 | Taylor ...................... | C03C 8/24 429/181 |
| 6,232,004 B1 | 5/2001 | Lasater | |
| 6,284,080 B1 | 9/2001 | Haq et al. | |
| 6,414,835 B1 | 7/2002 | Wolf et al. | |
| 6,579,492 B2 | 6/2003 | Wehler | |
| 6,586,675 B1 | 7/2003 | Bealka et al. | |
| 6,660,116 B2 | 12/2003 | Wolf et al. | |
| 7,068,491 B1 | 6/2006 | Burdon et al. | |
| 7,107,099 B1 | 9/2006 | O'Phelan et al. | |
| 7,222,419 B2 | 5/2007 | Horng et al. | |
| 7,480,988 B2 | 1/2009 | Ok et al. | |
| 7,569,452 B2 | 8/2009 | Fu et al. | |
| 7,668,597 B2 | 2/2010 | Engmark et al. | |
| 7,818,876 B2 | 10/2010 | Suaning | |
| 7,901,761 B1 | 3/2011 | Jiang et al. | |
| 7,930,032 B2 | 4/2011 | Teske et al. | |
| 7,970,474 B2 | 6/2011 | Starke | |
| 8,000,804 B1 | 8/2011 | Wessendorf et al. | |
| 8,155,743 B2 | 4/2012 | Rundle et al. | |
| 8,163,397 B2 | 4/2012 | Ok et al. | |
| 8,189,333 B2 | 5/2012 | Foster | |
| 8,494,635 B2 | 7/2013 | Troetzschel et al. | |
| 8,528,201 B2 | 9/2013 | Troetzschel et al. | |
| 8,755,887 B2 | 6/2014 | Troetzschel et al. | |
| 8,886,320 B2 | 11/2014 | Troetzschel et al. | |
| 8,929,987 B2 | 1/2015 | Troetzschel et al. | |
| 9,048,608 B2 | 6/2015 | Pavlovic | |
| 9,088,093 B2 | 7/2015 | Reisinger et al. | |
| 9,126,053 B2 | 9/2015 | Kempf et al. | |
| 9,129,747 B2 | 9/2015 | Pinwill et al. | |
| 9,407,076 B2 | 8/2016 | Troetzschel et al. | |
| 9,480,168 B2 | 10/2016 | Troetzschel et al. | |
| 2001/0018012 A1 | 8/2001 | Harmand et al. | |
| 2002/0166739 A1 | 11/2002 | Naerheim | |
| 2003/0109903 A1 | 6/2003 | Berrang et al. | |
| 2004/0023101 A1 | 2/2004 | Jacobson et al. | |
| 2004/0128016 A1 | 7/2004 | Stewart | |
| 2006/0025866 A1 | 2/2006 | Serafin, Jr. et al. | |
| 2006/0247714 A1 | 11/2006 | Taylor et al. | |
| 2007/0041164 A1 | 2/2007 | Greenberg et al. | |
| 2007/0217121 A1 | 9/2007 | Fu et al. | |
| 2007/0276389 A1 | 11/2007 | Franke et al. | |
| 2008/0060834 A1 | 3/2008 | Eck et al. | |
| 2009/0281586 A1 | 11/2009 | Lim | |
| 2010/0121438 A1 | 5/2010 | Jarvik | |
| 2011/0032658 A1 | 2/2011 | Iyer | |
| 2011/0034965 A1 | 2/2011 | Troetzschel et al. | |
| 2011/0034966 A1 | 2/2011 | Troetzschel et al. | |
| 2011/0048770 A1 | 3/2011 | Reiterer et al. | |
| 2011/0094768 A1 | 4/2011 | Davis et al. | |
| 2011/0186349 A1 | 8/2011 | Troetzschel et al. | |
| 2011/0190885 A1 | 8/2011 | Troetzschel et al. | |
| 2011/0232961 A1 | 9/2011 | Teske | |
| 2011/0232962 A1 | 9/2011 | Teske | |
| 2013/0299233 A1 | 11/2013 | Troetzschel et al. | |
| 2014/0008121 A1 | 1/2014 | Troetzschel et al. | |
| 2014/0144014 A1 | 5/2014 | Troetzschel et al. | |

OTHER PUBLICATIONS

The Final Office Action for U.S. Appl. No. 12/850,406 dated Feb. 25, 2013 (16 pages).
The Office Action for U.S. Appl. No. 12/850,406 dated Sep. 12, 2013 (16 pages).
The Dictionary definition of a cermet found at The Free Dictionary site http://www.thefreedictionary.com/cermets.
The Notice of Allowance for U.S. Appl. No. 12/850,406 dated Feb. 5, 2014 (9 pages).
The Office Action for U.S. Appl. No. 12/850,412 dated Sep. 17, 2012 (11 pages).
The Final Office Action for U.S. Appl. No. 12/850,412 dated Feb. 25, 2013 (18 pages).
The Office Action for U.S. Appl. No. 12/850,412 dated Sep. 11, 2013 (13 pages).
The Final Office Action for U.S. Appl. No. 12/850,412 dated Jan. 31, 2014 (8 pages).
The Restriction Requirement for U.S. Appl. No. 13/018,882 dated Dec. 20, 2012 (5 pages).
The Notice of Allowance for U.S. Appl. No. 13/018,882 dated May 10, 2013 (25 pages).
The Notice of Allowability for U.S. Appl. No. 13/018,882 dated Jul. 16, 2013 (6 pages).
The Office Action for U.S. Appl. No. 13/018,847 dated Dec. 5, 2012 (24 pages).
The Notice of Allowance for U.S. Appl. No. 13/018,847 dated Mar. 25, 2013 (25 pages).
The Office Action for U.S. Appl. No. 13/942,685 dated Dec. 23, 2013 (10 pages).
The Advisory Action for U.S. Appl. No. 12/850,412 dated Apr. 14, 2014 (3 pgs.).
The Office Action for U.S. Appl. No. 12/850,412 dated May 8, 2014 (11 pgs.).
The Notice of Allowance for U.S. Appl. No. 12/850,412 dated Sep. 2, 2014 (11 pgs.).
The Restriction Requirement for U.S. Appl. No. 14/023,096 dated Dec. 9, 2015 (7 pgs.).
The Final Office Action for U.S. Appl. No. 13/942,685 dated Apr. 14, 2014 (22 pgs.).
The Notice of Allowance for U.S. Appl. No. 13/942,685 dated Jul. 7, 2014 (5 pgs.).

(56) References Cited

OTHER PUBLICATIONS

The Notice of Allowance for U.S. Appl. No. 14/023,096 dated Mar. 28, 2016 (26 pgs.).
The Restriction Requirement for U.S. Appl. No. 14/171,275 dated Nov. 2, 2015 (6 pages).
The Office Action for U.S. Appl. No. 14/171,275 dated Feb. 24, 2016 (19 pages).
The Notice of Allowance for U.S. Appl. No. 14/171,275 dated Jul. 20, 2016 (7 pages).

* cited by examiner

METHOD OF PRODUCING A CERMET-CONTAINING BUSHING FOR AN IMPLANTABLE MEDICAL DEVICE

CROSS-REFERENCE TO RELATED APPLICATIONS

This application is a divisional of U.S. patent application Ser. No. 14/171,275, entitled "METHOD OF PRODUCING A CERMET-CONTAINING BUSHING FOR AN IMPLANTABLE MEDICAL DEVICE," having a filing date of Feb. 3, 2014, which claims priority to U.S. Pat. No. 8,755,887, issued Jun. 17, 2014, which claims priority to German Patent Application No. DE 10 2009 035 972.9, filed on Aug. 4, 2009, all of which are incorporated herein by reference.

BACKGROUND

One aspect relates to an electrical bushing for an implantable medical device having an annulus-like holding element for holding the electrical bushing in the implantable medical device, whereby the holding element includes a through-opening, at least one elongated conduction element extends through the through-opening, and an insulation element for forming a hermetic seal between the holding element and the conduction element is arranged in the through-opening. One aspect relates to a method for producing an electrical bushing for an implantable medical device.

DE 697 297 19 T2 describes an electrical bushing for an implantable electrical therapeutic device. Electrical bushings of this type serve to establish an electrical connection between a hermetically sealed interior and an exterior of said therapeutic device. Known implantable therapeutic devices include cardiac pacemakers or defibrillators, which usually include a hermetically sealed metal housing, which is provided with a connection body, also called header, on one side. Said connection body includes a connection socket for connecting electrode leads. In this context, the connection socket includes electrical contacts that serve to electrically connect electrode leads to the control electronics in the interior of the housing of the implantable therapeutic device—also called implantable device. An essential prerequisite for an electrical bushing of this type is hermetic sealing with respect to the surroundings.

Accordingly, it needs to be made sure that the conducting wires that are introduced into an insulation element and via which the electrical signals proceed, are introduced into the insulation element without any gaps. In this context, it has proven to be disadvantageous that the conducting wires in general are made of a metal and need to be introduced into a ceramic insulation element. In order to ensure long-lasting connection between the two elements, the internal surface of the bore hole in the insulation element must be metallized for soldering the conducting wires into them. Said metallization inside the bore hole in the insulation element has proven to be difficult to apply. Homogeneous metallization of the internal surface of the bore hole in the insulation element can be ensured only by means of expensive procedures.

Patent specification U.S. Pat. No. 5,769,874 describes an implantable electrical therapeutic device. Said therapeutic device includes a sealed area for a battery, whereby the area is provided with a coating. Said coating is to collect chemicals leaking from the battery. In this context, the coating can be made of a cermet.

For these and other reasons there is a need for the invention.

SUMMARY

One aspect is an electrical bushing for an implantable medical device, having an annulus-like holding element for holding the electrical bushing in the implantable medical device. The holding element includes a through-opening. At least one elongated conduction element extends through the through-opening. An insulation element for forming a hermetic seal between the holding element and the conduction element is arranged in the through-opening. The at least one conduction element includes components made of cermet.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
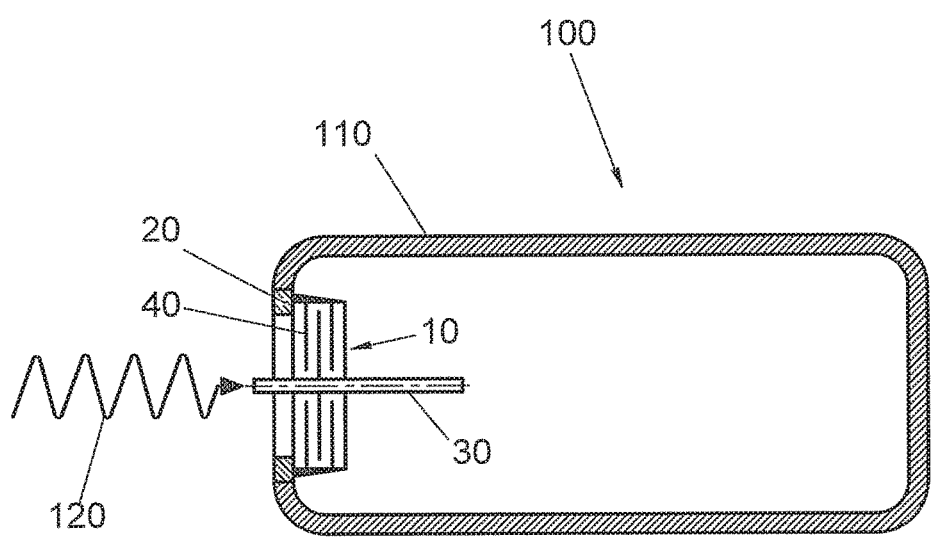
FIG. 1 illustrates an implantable medical device.

In the following Detailed Description, reference is made to the accompanying drawings, which form a part hereof, and in which is illustrated by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the invention. The following detailed description, therefore, is not to be taken in a limiting sense, and the scope of the invention is defined by the appended claims.

It is to be understood that the features of the various exemplary embodiments described herein may be combined with each other, unless specifically noted otherwise.

One aspect creates an electrical bushing for an implantable medical device, in which the aforementioned disadvantages are avoided, and in which a long-lasting sealing connection between insulation element and conduction element is ensured. One aspect is an electrical bushing for an implantable medical device and one aspect is a method for producing an electrical bushing for an implantable medical device. Any features and details that are described in this context in relation to the electrical bushing or the implantable medical device shall also apply in relation to the method, and vice versa.

The electrical bushing according to one embodiment is characterized in that the at least one insulation element includes a cermet.

According to the prior art, the conduction element is a metallic wire. In contrast, in one embodiment, the conduction element is a cermet, that is, a composite material made of ceramic materials in a metallic matrix. A conduction element designed as described is easy to connect to the insulation element since it is a ceramic material. Accordingly, it is feasible to generate green compacts of both the conduction element and the insulation element which are subsequently subjected to a sintering process. The resulting electrical bushing is not only biocompatible and resistant, but also illustrates good hermetic sealing. No fissures or connecting sites still needing to be soldered arise between the conduction element and the insulation element. Rather, sintering results in connection of the insulation element and the conduction element. A development of an embodiment therefore provides the at least one conduction element to consist of a cermet. The conduction element in one development does not only includes components made of cermet, but is fully made of a cermet.

In the context of one embodiment, the terms, "cermet" or "cermet-containing", shall refer to all composite materials made of ceramic materials in a metallic matrix (binding agent). These are characterized by their particularly high hardness and wear resistance. The "cermets" and/or "cermet-containing" substances are cutting materials that are related to hard metals, but contain no tungsten carbide hard metal and are produced by powder metallurgical means. A sintering process for cermets and/or the cermet-containing bearing element proceeds just like with homogeneous powders with the exception that the metal is compacted more strongly at the same pressing force as compared to the ceramic material. The cermet-containing bearing element has a higher thermal shock and oxidation resistance than sintered hard metals. In most cases, the ceramic components of the cermet are aluminum oxide ($Al_2O_3$) and zirconium dioxide ($ZrO_2$), whereas niobium, molybdenum, titanium, cobalt, zirconium, chromium are conceivable as metallic components.

In the context of one embodiment, the term, "comprising a cermet", refers to a mixture of materials in which a part of the material of the conduction element or other element is connected to a cermet. Accordingly, this is understood to mean that the corresponding element is cermet-containing. It can be formed and fired from a cermet-containing material and/or powder. This scope also encompasses a development, in which the element consists of a cermet. In this variant, the corresponding element—such as conduction element or the holding element to be illustrated below—are completely made of a cermet.

In order to integrate the electrical bushing into the housing of a cardiac pacemaker, the electrical bushing includes a holding element. Said holding element is arranged in annulus-like manner around the insulation element. The holding element serves for connection to the housing in a non-positive or positive-type fit. For this purpose, a media-tight connection must arise between the holding element and the housing. In one development, the electrical bushing includes a holding element that includes a cermet. The cermet-containing holding element can be connected to the housing of the implantable medical device in a simple, long-lasting, and hermetically sealing manner.

A further embodiment has the holding element not comprise a cermet, but consist of a cermet. Moreover, it is conceivable that the conduction element and the holding element are made of the same material. In this variant, the same materials are used for the conduction element and the holding element. In one embodiment, this concerns a resistant, conductive, and biocompatible cermet. Since both the holding element and the conduction element are still to be connected to metallic components, both must include the corresponding prerequisites for welding or soldering. If a cermet is found that meets the specified prerequisites, it can be utilized for both the holding element and for the conduction element in order to thus obtain a particularly inexpensive electrical bushing.

One embodiment includes an insulation element that is made from an insulating composition of materials. The insulation element serves to insulate the conducting wire from the holding element and any other objects of the implantable medical device. Electrical signals proceeding through the conducting wire are not to be attenuated or short-circuited by contacting the housing of the implantable device. Moreover, the insulation element must include a biocompatible composition in order to be implanted medically. For this reason, it is preferred in one embodiment for the insulation element to consist of a glass-ceramic or glass-like material. It has proven to be preferred in one embodiment for the insulating composition of materials of the insulation element to be at least one from the group of aluminum oxide ($Al_2O_3$), magnesium oxide (MgO), zirconium oxide ($ZrO_2$), aluminum-titanate ($Al_2TiO_5$), and piezo-ceramics. The aluminum oxide ceramic material has a high electrical resistance and low dielectric losses. Moreover, these properties are supplemented by the high thermal resistance as well as good biocompatibility.

Another development of the bushing according to one embodiment is characterized in that the holding element includes at least one flange, whereby, in particular, the flange is conductive like a metal. The flange serves to seal the electrical bushing with respect to a housing of the implantable device. The holding element holds the electrical bushing in the implantable device. In the development described at present, the holding element includes at least one flange on one external surface. Said flanges form a bearing, which can be engaged by the lids of the implantable medical device, in one embodiment can be engaged in a sealing manner. Accordingly, the holding element with flanges attached to it can have a U- or H-shaped cross-section. Integrating at least one flange into the holding element ensures safe, impact-proof, and long-lasting integration of the electrical bushing into the implantable device. In addition, the flanges can be designed such that the lids of the implantable device are connected clip-like to the holding element in a non-positive fit- and/or positive fit-like manner.

Another development of the electrical bushing according to one embodiment is characterized in that the at least one flange includes a cermet. In the scope of this development, both the holding element and the flange include a cermet. In one embodiment, flange and holding element are made of the same material. Designing the flange as cermet allows it to be sintered easily and inexpensively as part of the holding element and jointly with the insulation element and the conduction element in the scope of the method to be described below.

One embodiment uses at least one cermet-containing conduction element in an electrical bushing for an implantable medical device. In this context, any features and details that were described in relation to the electrical bushing and/or the method shall also apply in relation to the use of a cermet-containing bearing element.

Another embodiment is an implantable medical device, for example, a cardiac pacemaker or defibrillator, having an electrical bushing according to any one of the embodiments described above. In this context, any features and details that were described in relation to the electrical bushing and/or the method shall also apply in relation to the implantable medical device.

One embodiment also relates to a method for producing an electrical bushing for an implantable medical device. Some disadvantages arising during the production of electrical bushings have been described above. The objective resulting therefrom has also been specified above. According to one embodiment, the method for producing an electrical bushing for an implantable medical device includes the following steps:
  a. generating an insulation element green compact for an insulation element from an insulating composition of materials;
  b. forming at least one cermet-containing conduction element green compact for a conduction element;
  c. introducing the at least one conduction element green compact into the insulation element green compact;
  d. firing the insulation element green compact and the at least one conduction element green compact to obtain an insulation element with at least one conduction element.

Any features and details that are described in this context in relation to the electrical bushing shall also apply in relation to the method according to the embodiment, and vice versa.

One special feature of the method according to one embodiment results from both the insulation element and the conduction element comprising ceramic components which are processed by means of a sintering procedure. According to procedural step a), an insulation element green compact is formed from an insulating composition of materials. This can be effected by pressing together the composition of materials in a mold. For this purpose, the insulating composition of materials is a powder mass whose powder particles illustrate at least a minimum of cohesion. This is commonly effected in that a grain size of the powder particles does not exceed 0.5 mm. In this context, the production of a green compact is effected either by pressing powder masses or by forming and subsequent drying. Procedural steps of this type are also used to form the cermet-containing conduction element green compact.

One embodiment provides the powder that is pressed into the conduction element green compact to be cermet-containing or to consist of a cermet. Subsequently, the two green compacts—the insulation element green compact and the conduction element green compact—are placed together. After this step, called step c), the two green compact are fired—which is also called sintering. In the process, the green compacts are subjected to a heat treatment below the melting temperature of the powder particles of the green compact. In the process, the porosity and the volume of the green compacts are decreased markedly. Accordingly, a special feature of the embodiment is that the insulation element and the conduction element are fired jointly. There is no subsequent need for connection of the two elements any more. The firing process effects connection of the conduction element to the insulation element that is of the non-positive fit- and/or positive fit- and/or substance-to-substance-type. Thus, hermetically sealed integration of the conduction element into the insulation element is achieved.

There is no need for subsequent soldering or welding of the conduction element in the insulation element. Rather, the joint firing and the use of a cermet-containing green compact effects a hermetically sealed connection between the insulation element and the conduction element.

One development of the method according to one embodiment is characterized in that step a) includes a partial sintering of the insulation element green compact. As part of said only partial sintering, the green compact of the insulation element is heat treated. This is already associated with some shrinkage of the volume of the insulation element green compact. But the volume of the green compact does not reach its final stage. Rather, another heat treatment as part of step d) is required, in which the insulation element green compact and the conduction element green compact are shrunk to their final size. In said development, the green compact is heat treated only partly in order to already attain a certain surface hardness to render the handling of the green compact of the insulation element easier. This is expedient, for example, in the case of insulating compositions of materials which can be pressed into the form of a green compact only with some difficulty.

Another development is characterized in that the conduction element green compact is also already partly sintered in step b). As described above for the insulation element green compact, the conduction element green compact can also be sintered to some extent in order to already attain a certain surface stability. It needs to be noted in this context that the final, complete sintering in this development also does not occur until step d). Consequently, the conduction element green compact also attains its final size only in step d).

Another development of the method is characterized in that the method includes the following steps preceding step d):
  producing a cermet-containing holding element green compact for a holding element;
  introducing the at least one bearing element green compact into the insulation element green compact, and introducing the insulation element green compact into the holding element green compact;
  whereby step d) includes:
  d. firing the insulation element green compact and the at least one bearing element green compact and the holding element green compact to obtain an insulation element with at least one bearing element and a holding element.

The special feature of this procedural step is that, aside from the bearing element green compact and the insulation element green compact, the bearing element green compact is also sintered in one step. All three green compacts are generated, then joined, and subsequently fired and/or sintered as a unit. In one development, the production of the at least one cermet-containing holding element green compact can include partial sintering. In this context, the fringe green compact is again provided to be partly sintered in order to attain higher surface stability.

FIG. 1 illustrates, in an exemplary fashion, an implantable device 100, such as, for example, a cardiac pacemaker, with an electrical bushing 10 being integrated into the metallic housing thereof. The electrical bushing 10 is connected to the housing 110 of the implantable device 100 in a hermetically sealed manner, for example, by means of welding. In one example, it is therefore advantageous for a holding element 20 of the electrical bushing 10 to include a metal that can be welded to the housing 110 both easily and reliably. The electrical bushing 10 serves to establish an electrical connection between the hermetically sealed interior of the medical device 100 and the exterior.

Accordingly, a conducting coil 120, which is indicated only schematically herein and is connected to an stimulation electrode, can be attached to the electrical bushing 10. Stimulation electrodes of this type are used, for example, in heart muscles in order to allow signals of the cardiac pacemaker to be conducted to the muscle. In order to attain hermetic sealing, the conducting wire 30 is embedded into an insulation element 40. The insulation element 40 leads to the formation of a hermetic seal between the holding element 20 and the at least one conducting wire 30 in a through-opening 22 that is formed by the annulus-like holding element 20. The electrically insulating insulation element prevents short-circuiting between the electrically conductive elongated conducting wire 30 and the metallic housing 110 and/or the metallic holding element 20.

Figure 2:
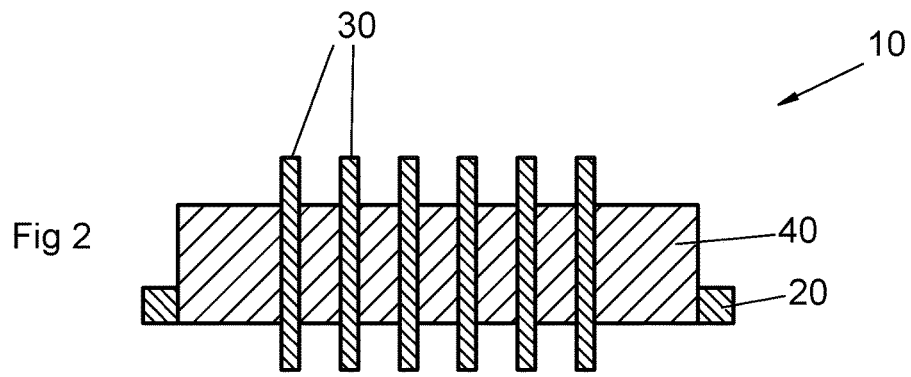
FIG. 2 illustrates a drawing of a section through an electrical bushing according with one embodiment.

In electrical bushings according to the prior art, a metallic wire is used as conduction element and needs to be soldered into an insulation element. For this purpose, the insulation element includes a cylinder-like bushing for the conduction element, with said bushing being provided with a metallic coating on its internal wall. Soldering has proven to be error-prone and expensive. FIG. 2 illustrates an electrical bushing 10 according to one embodiment that overcomes the disadvantages mentioned above.

Figure 3:
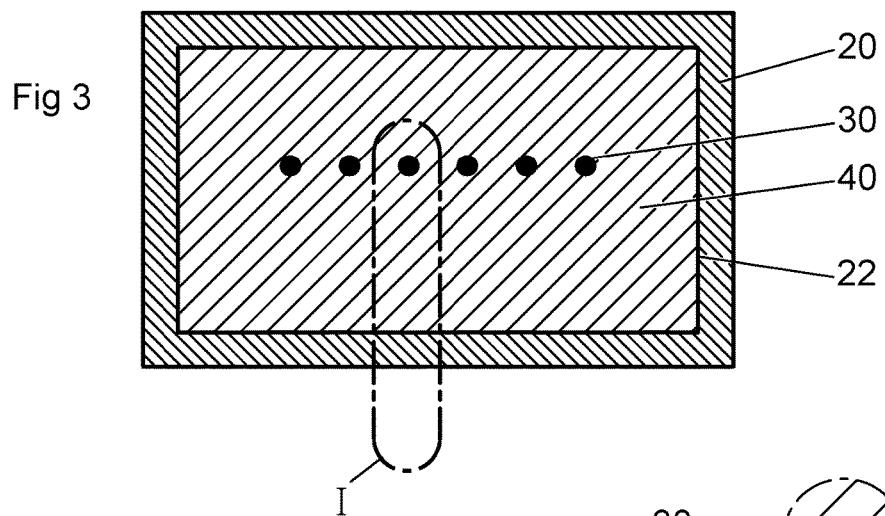
FIG. 3 illustrates a schematic top view onto the electrical bushing according to FIG. 2.

In one embodiment, the electrical bushing 10 includes an annulus-like holding element 20. The holding element 20 serves to hold the electrical bushing 10 in the implantable medical device 100. The holding element 20, designed to be annulus-like, includes a through-opening 22. This is particularly evident from FIG. 3, which illustrates a top view onto the electrical bushing 10 illustrated in a section in FIG. 2. Designed rectangular in shape and annulus-like, the holding element 20 possesses, on its interior, the through-opening 22, which is designed to be rectangular in the present case. At least one elongated conduction element 30 extends through said through-opening 22. In the exemplary embodiment illustrated, a total of six conduction elements 30 extend through the holding element 20. An insulation element 40 is arranged in the through-opening 22 such that hermetic sealing is effected between the holding element 20 and the conduction element 30. The special feature, according to one embodiment, of the electrical bushing 10 illustrated results from the conduction element 30 comprising a cermet or consisting of a cermet.

A cermet is a composite material made of ceramic materials in a metallic matrix. The special feature of a cermet-containing conduction element 30 of this type is that it can be sintered in a single procedural step jointly with the also ceramic-containing insulation element 40. Thus, no undesirable through-openings, fissures or imperfections arise between conduction element 30 and insulation element 40 anymore. Rather, a media-tight connection is created between the two elements 40, 30. The individual procedural steps for producing an electrical bushing 10 according to one embodiment, are as follows:

a. generating an insulation element green compact for an insulation element (40) from an insulating composition of materials;

b. forming at least one cermet-containing conduction element green compact for a conduction element (30);

c. introducing the at least one conduction element green compact into the insulation element green compact;

d. firing the insulation element green compact and the at least one conduction element green compact to obtain an insulation element (40) with at least one conduction element (30).

The special feature of the method according to the embodiment results from both the insulation element green compact and the conduction element green compact, each being pressed from powders and subsequently being fired. It is therefore feasible in few procedural steps to generate a green compact that include both the conduction element green compact and the insulation element green compact and subsequently fire said total green compact. In one development, not only the insulation element 40 and the conduction element 30, but also the holding element 20, are pressed from powders and sintered.

Accordingly, the holding element 20 is also produced from a cermet-containing powder in one production step. Subsequently, the three green compacts—holding element 20, conduction element 30, insulation element 40—are placed together. This results in the electrical bushing 10 in a green compact stage. Subsequently, the three green compacts are fired jointly. The electrical bushing 10 resulting therefrom, on the one hand, meets all requisite electrical requirements and, on the other hand, is produced in one step with no need for subsequent soldering or welding of individual elements. Moreover, the metal-containing, a cermet-comprising holding element 20 facilitates simple, long-lasting connection to the housing of the implantable medical device 100.

Figure 4:
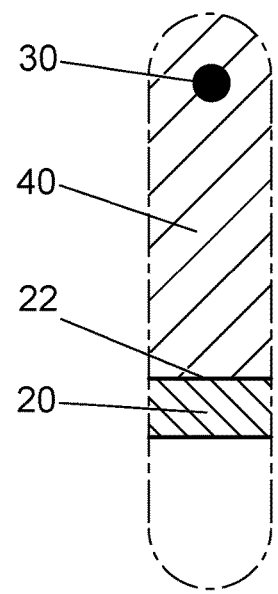
FIG. 4 illustrates a detail magnification of the electrical bushing.

FIG. 4 again illustrates the individual components of the electrical bushing 10, in magnification. This is a detail magnification of the region of FIG. 3 denoted I. Made from an electrically insulating composition of materials, the insulation element 40 surrounds the conduction element 30. For example, conducting coils for a cardiac pacemaker can be attached to said conduction element 30. The insulation element 40 is surrounded by a holding element 20 that is designed to be annulus-like. Said holding element 20 is cermet-containing in the development illustrated.

The holding element 20 can include a flange for integration of the electrical bushing 10 in the implantable medical device 100. A flange is not shown in the figures. A housing 110 of the device 100 can touch against the flange in order to thus facilitate a hermetically sealed connection between both elements. In one embodiment, the holding element 20 and the flange are made of the same material and/or in the form of a single part.

Although specific embodiments have been illustrated and described herein, it will be appreciated by those of ordinary skill in the art that a variety of alternate and/or equivalent implementations may be substituted for the specific embodiments shown and described without departing from the scope of the invention. This application is intended to cover any adaptations or variations of the specific embodiments discussed herein. Therefore, it is intended that this invention be limited only by the claims and the equivalents thereof.

What is claimed is:

1. A method for producing an electrical bushing for an implantable medical device, the method comprising:

forming a holding element for holding the electrical bushing in the implantable medical device, the holding element comprising a through-opening;

forming an insulation element comprising aluminum oxide within the through-opening;

forming at least one elongated conduction element extending through insulation element, the at least one elongated conduction element comprising an aluminum oxide in a metallic matrix; and jointly firing the insulation element and the at least one elongated conduction element thereby forming a hermetic seal therebetween without welding or soldering;

wherein prior to jointly firing the insulation element and the at least one elongated conduction element and prior to forming the at least one elongated conduction element extending through the insulation element, partially sintering at least one of the insulation element and the at least one elongated conduction element to achieve a surface hardness such that handling the conduction element or insulation element is improved.

2. The method according to claim 1, wherein forming the insulation element further comprises generating an insulation element green compact for forming the insulation element and wherein forming the at least one elongated conduction element comprises forming at least one cermet-containing conduction element green compact for forming the conduction element.

3. The method according to claim 2, wherein jointly firing the insulation element and the at least one elongated conduction element comprises jointly firing the insulation element green compact and the conduction element green compact.

4. The method according to claim 1, wherein the holding element comprises a cermet.

5. The method of claim 1 further comprising forming the conduction element and the holding element from the same material.

6. A method for producing an implantable medical device, the method comprising:
   forming a holding element for holding an electrical bushing in the implantable medical device, the holding element comprising a through-opening;
   forming an insulation element comprising aluminum oxide within the through-opening;
   forming at least one elongated conduction element extending through insulation element, the at least one elongated conduction element comprising an aluminum oxide in a metallic matrix; and
   jointly firing the insulation element and the at least one elongated conduction element thereby forming a hermetic seal therebetween without welding or soldering;
   wherein prior to jointly firing the insulation element and the at least one elongated conduction element and prior to forming the at least one elongated conduction element extending through the insulation element, partially sintering at least one of the insulation element and the at least one elongated conduction element to achieve a surface hardness such that handling the conduction element or insulation element is improved.

7. The method according to claim 6, wherein forming the insulation element further comprises generating an insulation element green compact for forming the insulation element and wherein forming the at least one elongated conduction element comprises forming at least one cermet-containing conduction element green compact for forming the conduction element.

8. The method according to claim 7, wherein jointly firing the insulation element and the at least one elongated conduction element comprises jointly firing the insulation element green compact and the conduction element green compact.

9. The method according to claim 6, wherein the holding element comprises a cermet.

10. The method of claim 6 further comprising forming the conduction element and the holding element from the same material.

* * * * *